(12) United States Patent
Benvegnu et al.

(10) Patent No.: US 8,563,335 B1
(45) Date of Patent: Oct. 22, 2013

(54) METHOD OF CONTROLLING POLISHING USING IN-SITU OPTICAL MONITORING AND FOURIER TRANSFORM

(75) Inventors: Dominic J. Benvegnu, La Honda, CA (US); Boguslaw A. Swedek, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 13/454,002

(22) Filed: Apr. 23, 2012

(51) Int. Cl.
*H01L 21/66* (2006.01)

(52) U.S. Cl.
USPC .......... 438/16; 438/8; 438/692; 257/E21.304; 257/E21.23; 257/E21.53; 216/84; 216/85; 216/87

(58) Field of Classification Search
USPC .......... 438/8, 16, 692; 257/E21.304, E21.23, 257/E21.53; 216/84, 85, 87
See application file for complete search history.

(56) References Cited

U.S. PATENT DOCUMENTS

| | | | |
|---|---|---|---|
| 6,204,922 B1 * | 3/2001 | Chalmers | 356/630 |
| 6,664,557 B1 | 12/2003 | Amartur | |
| 6,991,514 B1 * | 1/2006 | Meloni et al. | 451/5 |
| 7,101,799 B2 | 9/2006 | Paik | |
| 7,160,739 B2 | 1/2007 | Shanmugasundram et al. | |
| 2007/0042675 A1 | 2/2007 | Benvegnu et al. | |
| 2007/0128827 A1 * | 6/2007 | Faris | 438/455 |
| 2007/0224915 A1 | 9/2007 | David et al. | |
| 2008/0099443 A1 | 5/2008 | Benvegnu et al. | |
| 2008/0274670 A1 | 11/2008 | Tada et al. | |
| 2011/0281501 A1 | 11/2011 | Qian et al. | |
| 2011/0316166 A1 * | 12/2011 | Yu et al. | 257/774 |

OTHER PUBLICATIONS

International Search Report and Written Opinion in International Application No. PCT/US2013/034500, mailed Jul. 10, 2013, 14 pages.

* cited by examiner

*Primary Examiner* — Bac Au
*Assistant Examiner* — Victor Barzykin
(74) *Attorney, Agent, or Firm* — Fish & Richardson P.C.

(57) ABSTRACT

A method of controlling a polishing operation includes polishing a substrate, during polishing obtaining a sequence over time of measured spectra from the substrate with an in-situ optical monitoring system, for each measured spectrum from the sequence of measured spectra applying a Fourier transform to the measured spectrum to generate a transformed spectrum thus generating a sequence of transformed spectra, for each transformed spectrum identifying a peak of interest from a plurality of peaks in the transformed spectrum, for each transformed spectrum determining a position value for the peak of interest in the transformed spectrum thus generating a sequence of position values, and determining at least one of a polishing endpoint or an adjustment of a pressure to the substrate from the sequence of position values.

17 Claims, 9 Drawing Sheets

METHOD OF CONTROLLING POLISHING USING IN-SITU OPTICAL MONITORING AND FOURIER TRANSFORM

TECHNICAL FIELD

The present disclosure relates to optical monitoring during chemical mechanical polishing of substrates.

BACKGROUND

An integrated circuit is typically formed on a substrate by the sequential deposition of conductive, semiconductive, or insulative layers on a silicon wafer. A variety of fabrication processes require planarization of a layer on the substrate. For example, for certain applications, e.g., polishing of a metal layer to form vias, plugs, and lines in the trenches of a patterned layer, an overlying layer is planarized until the top surface of a patterned layer is exposed. In other application, e.g., planarization of a dielectric layer for photolithography, an overlying layer is polished until a desired thickness remains over the underlying layer.

Chemical mechanical polishing (CMP) is one accepted method of planarization. This planarization method typically requires that the substrate be mounted on a carrier or polishing head. The exposed surface of the substrate is typically placed against a rotating polishing pad. The carrier head provides a controllable load on the substrate to push it against the polishing pad. Abrasive polishing slurry is typically supplied to the surface of the polishing pad.

One problem in CMP is determining whether the polishing process is complete, i.e., whether a substrate layer has been planarized to a desired flatness or thickness, or when a desired amount of material has been removed. Variations in the slurry distribution, the polishing pad condition, the relative speed between the polishing pad and the substrate, and the load on the substrate can cause variations in the material removal rate. These variations, as well as variations in the initial thickness of the substrate layer, cause variations in the time needed to reach the polishing endpoint. Therefore, determining the polishing endpoint merely as a function of polishing time can lead to within-wafer non-uniformity (WIWNU) and wafer-to-wafer non-uniformity (WTWNU).

In some systems, a substrate is optically monitored in-situ during polishing, e.g., through a window in the polishing pad. However, existing optical monitoring techniques may not satisfy increasing demands of semiconductor device manufacturers.

SUMMARY

Some polishing processes involve polishing of thick semiconductor or dielectric layers, e.g., layers that are 2 to 200 µm thick. Unfortunately, many optical monitoring techniques are not reliable for such thick layers. One approach to optical monitoring that may be able to reliably measure thickness of thick layers, but which may also be applicable to thinner layers, is to measure a spectrum of light reflected from the substrate, perform a Fourier transform of the reflected spectrum, and track one of the peaks in the Fourier space.

In one aspect, a method of controlling a polishing operation includes polishing a substrate, during polishing obtaining a sequence over time of measured spectra from the substrate with an in-situ optical monitoring system, for each measured spectrum from the sequence of measured spectra applying a Fourier transform to the measured spectrum to generate a transformed spectrum thus generating a sequence of transformed spectra, for each transformed spectrum identifying a peak of interest from a plurality of peaks in the transformed spectrum, for each transformed spectrum determining a position value for the peak of interest in the transformed spectrum thus generating a sequence of position values, and determining at least one of a polishing endpoint or an adjustment of a pressure to the substrate from the sequence of position values.

Implementations can include on or more of the following features. Obtaining the sequence of measured spectra may include directing a beam of near infrared light onto the substrate and measuring a spectrum of a reflection of the beam. The beam of near infrared light may include light having a wavelength of 0.9 to 1.7 µm. Polishing the substrate may be polishing step in fabrication of a through silicon via. Polishing the substrate may include polishing a silicon layer of a multilayer substrate, the multilayer substrate including a semiconductor wafer and an adhesive layer bonding the silicon layer to the semiconductor wafer. Polishing the substrate may include polishing an overlying first layer of a multilayer substrate, the multilayer substrate including an underlying second layer and a third layer, the second layer between the first layer and the third layer. The first layer may have a thickness greater than two microns. Applying a Fourier transform may include applying a fast Fourier transform. The measured spectrum may be a spectrum of intensity as a function of inverse wavelength and the transformed spectrum may be a spectrum of intensity as a function of length. Selecting the peak of interest may include identifying a highest peak and a second-highest peak within a range of position values, and determining a height and a position for each of the highest peak and a second-highest peak. Selecting the peak of interest may include determining whether the highest peak has a lower position value than the second-highest peak. Selecting the peak of interest may include determining that highest peak has a lower position value than the second-highest peak and selecting the highest peak as the peak of interest. Selecting the peak of interest may include determining whether the height of the second-highest peak is within a threshold of the height of the highest peak. Selecting the peak of interest may include determining that highest peak has a higher position value than the second-highest peak and that the height of the second-highest peak is above a threshold of the height of the highest peak and selecting the highest peak as the peak of interest. Selecting the peak of interest may include determining that highest peak has a higher position value than the second-highest peak and that the height of the second-highest peak is below a threshold of the height of the highest peak and selecting second-highest peak as the peak of interest. The position value may be in units of length, e.g., may be a thickness value.

In another aspect, a non-transitory computer program product, tangibly embodied in a machine readable storage device, includes instructions to carry out the method.

Implementations may optionally include one or more of the following advantages. The thickness of a thick semiconductor or dielectric layer can be reliably measured in-situ. The thickness of a selected layer can be determined in the presence of multiple layers in a stack. Thickness monitoring can be performed during the polishing step of a through silicon via (TSV) application. Reliability of the endpoint system to detect a desired polishing endpoint can be improved, and within-wafer and wafer-to-wafer thickness non-uniformity (WIWNU and WTWNU) can be reduced.

The details of one or more implementations are set forth in the accompanying drawings and the description below. Other aspects, features, and advantages will be apparent from the description and drawings, and from the claims.

BRIEF DESCRIPTION OF THE DRAWINGS

Like reference numbers and designations in the various drawings indicate like elements.

DETAILED DESCRIPTION

One optical monitoring technique is to measure a spectrum of light reflected from a substrate during polishing. One potential problem is that some techniques for analyzing the spectrum are not reliable for thick layers, e.g., semiconductor or dielectric layers that are 2 to 200 µm thick, or for substrates that include stacks of multiple layers.

An example of an application that can introduce these problems is polishing during fabrication of a through-silicon via (TSV). A TSV is a vertical electrical connection (via) passing completely through a silicon substrate. One step in TSV formation is polishing of the back-side of the silicon substrate until copper (Cu) pillars are exposed (the polishing occurs when the wafer is not yet diced, so-called Si—Cu via reveal, or Oxide-Cu via reveal when oxide deposition is applied after Cu via recess etch.

A spectral analysis technique that might address these problems is to perform a Fourier transform of the reflected spectrum, and track one of the peaks in the Fourier space. In addition, the reflected spectrum can be generated using near-infrared (NIR) light rather than visible light.

Figure 1:
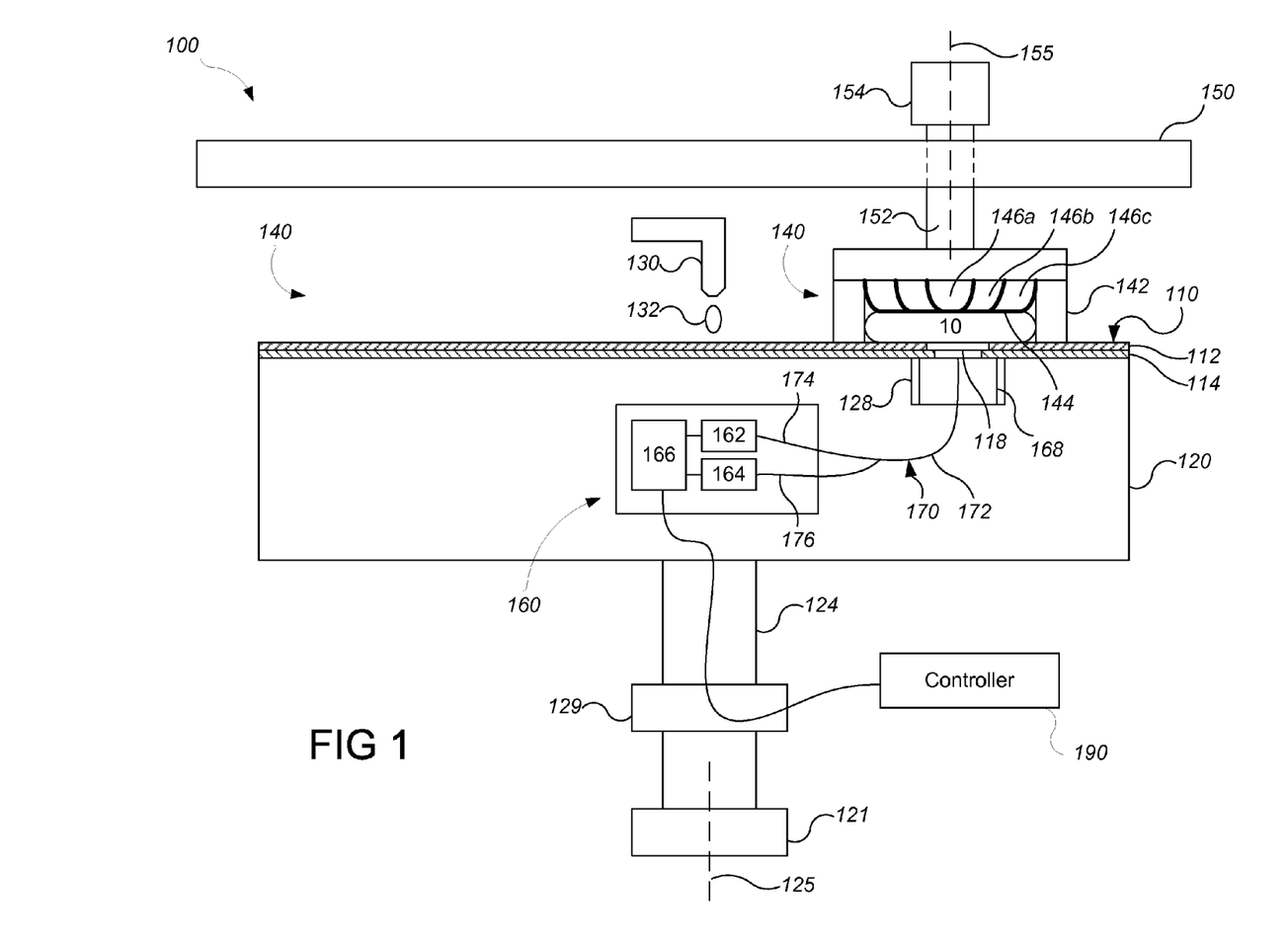
FIG. 1 illustrates a schematic cross-sectional view of an example of a polishing apparatus.

FIG. 1 illustrates an example of a polishing apparatus 100. The polishing apparatus 100 includes a rotatable disk-shaped platen 120 on which a polishing pad 110 is situated. The platen is operable to rotate about an axis 125. For example, a motor 121 can turn a drive shaft 124 to rotate the platen 120. The polishing pad 110 can be a two-layer polishing pad with an outer polishing layer 112 and a softer backing layer 114.

The polishing apparatus 100 can include a port 130 to dispense polishing liquid 132, such as a slurry, onto the polishing pad 110. The polishing apparatus can also include a polishing pad conditioner to abrade the polishing pad 110 to maintain the polishing pad 110 in a consistent abrasive state.

The polishing apparatus 100 includes at least one carrier head 140. The carrier head 140 is operable to hold a substrate 10 against the polishing pad 110. The carrier head 140 can have independent control of the polishing parameters, for example pressure, associated with each respective substrate.

In particular, the carrier head 140 can include a retaining ring 142 to retain the substrate 10 below a flexible membrane 144. The carrier head 140 also includes a plurality of independently controllable pressurizable chambers defined by the membrane, e.g., three chambers 146a-146c, which can apply independently controllable pressurizes to associated zones on the flexible membrane 144 and thus on the substrate 10. Although only three chambers are illustrated in FIG. 1 for ease of illustration, there could be one or two chambers, or four or more chambers, e.g., five chambers.

The carrier head 140 is suspended from a support structure 150, e.g., a carousel, and is connected by a drive shaft 152 to a carrier head rotation motor 154 so that the carrier head can rotate about an axis 155. Optionally the carrier head 140 can oscillate laterally, e.g., on sliders on the carousel 150; or by rotational oscillation of the carousel itself. In operation, the platen is rotated about its central axis 125, and the carrier head is rotated about its central axis 155 and translated laterally across the top surface of the polishing pad.

While only one carrier head 140 is shown, more carrier heads can be provided to hold additional substrates so that the surface area of polishing pad 110 may be used efficiently.

The polishing apparatus also includes an in-situ optical monitoring system 160, e.g., a spectrographic monitoring system, which can be used to determine whether to adjust a polishing rate or an adjustment for the polishing rate as discussed below. An optical access through the polishing pad is provided by including an aperture (i.e., a hole that runs through the pad) or a solid window 118. The solid window 118 can be secured to the polishing pad 110, e.g., as a plug that fills an aperture in the polishing pad, e.g., is molded to or adhesively secured to the polishing pad, although in some implementations the solid window can be supported on the platen 120 and project into an aperture in the polishing pad.

The optical monitoring system 160 can include a light source 162, a light detector 164, and circuitry 166 for sending and receiving signals between a remote controller 190, e.g., a computer, and the light source 162 and light detector 164. One or more optical fibers can be used to transmit the light from the light source 162 to the optical access in the polishing pad, and to transmit light reflected from the substrate 10 to the detector 164. For example, a bifurcated optical fiber 170 can be used to transmit the light from the light source 162 to the substrate 10 and back to the detector 164. The bifurcated optical fiber an include a trunk 172 positioned in proximity to the optical access, and two branches 174 and 176 connected to the light source 162 and detector 164, respectively.

In some implementations, the top surface of the platen can include a recess 128 into which is fit an optical head 168 that holds one end of the trunk 172 of the bifurcated fiber. The optical head 168 can include a mechanism to adjust the vertical distance between the top of the trunk 172 and the solid window 118.

The output of the circuitry 166 can be a digital electronic signal that passes through a rotary coupler 129, e.g., a slip ring, in the drive shaft 124 to the controller 190 for the optical monitoring system. Similarly, the light source can be turned on or off in response to control commands in digital electronic signals that pass from the controller 190 through the rotary coupler 129 to the optical monitoring system 160. Alternatively, the circuitry 166 could communicate with the controller 190 by a wireless signal.

The light source 162 can be operable to emit near-infrared (NIR) light. In one implementation, the NIR light emitted includes light having wavelengths of 0.9 to 1.7 µm.

Figure 2:
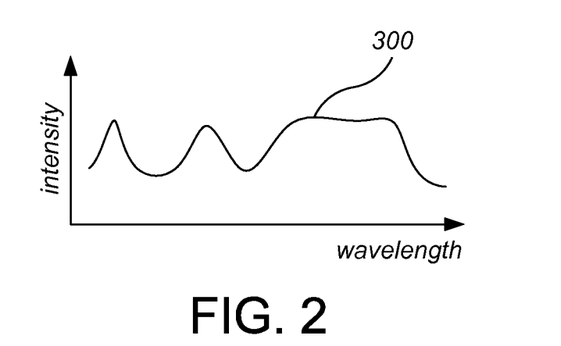
FIG. 2 illustrates a measured spectrum from the in-situ optical monitoring system.
Figure 3:
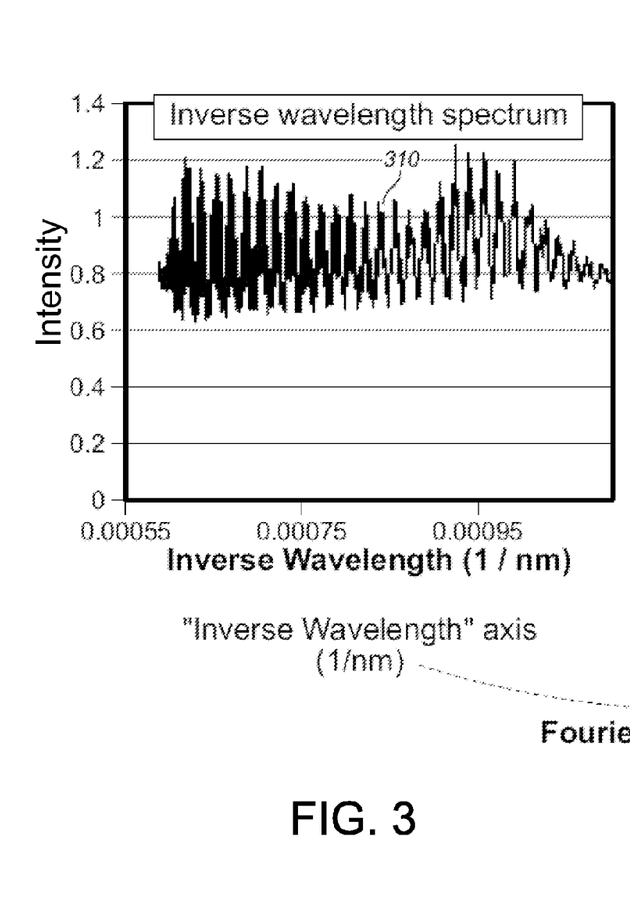
FIG. 3 illustrates measured spectrum in inverse wavelength (wavenumber) space.

The light detector 164 can be a spectrometer. A spectrometer is an optical instrument for measuring intensity of light over a portion of the electromagnetic spectrum. A suitable spectrometer is a grating spectrometer. Typical output for a spectrometer is the intensity of the light as a function of wavelength (or frequency). FIG. 2 illustrates an example of a measured spectrum 300 with intensity as a function of wavelength. FIG. 3 illustrates an example of a measured spectrum 310 with intensity as a function inverse wavelength, e.g., as a function of wavenumber. If necessary, the controller 190 can convert a measured spectrum 300 with intensity as a function of wavelength to a measured spectrum 310 with intensity as a function of inverse wavelength. A measured spectrum with intensity as a function of inverse wavelength is also referred to below as an inverse wavelength spectrum.

As noted above, the light source 162 and light detector 164 can be connected to a computing device, e.g., the controller 190, operable to control their operation and receive their signals. The computing device can include a microprocessor situated near the polishing apparatus, e.g., a programmable computer. With respect to control, the computing device can, for example, synchronize activation of the light source with the rotation of the platen 120.

The optical monitoring system 160 is configured to generate a sequence of measured spectra at a measurement frequency. In some implementations, the light source 162 and detector 164 of the in-situ monitoring system 160 are installed in and rotate with the platen 120. In this case, the measurement frequency can be once per rotation of the platen. It is possible for multiple spectra to be obtained as the optical access passes below the substrate 10, in which case one of the obtained spectra can be selected, or multiple obtained spectra can be combined, to provide the measured spectra.

In operation, the controller 190 can receive, for example, a signal that carries information describing a spectrum of the light received by the light detector for a particular flash of the light source or time frame of the detector. Thus, this spectrum is a spectrum measured in-situ during polishing.

Without being limited to any particular theory, the spectrum of light reflected from the substrate 10 evolves as polishing progresses (e.g., over multiple rotations of the platen, not during a single sweep across the substrate) due to changes in the thickness of the outermost layer, thus yielding a sequence of time-varying spectra. Moreover, particular spectra are exhibited by particular thicknesses of the layer stack.

Figure 4:
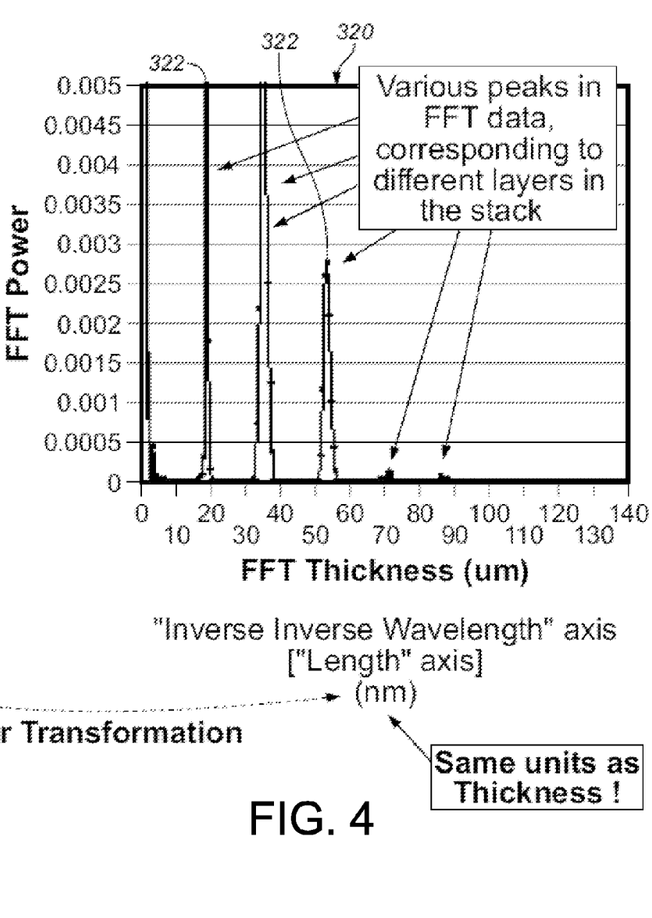
FIG. 4 illustrates a Fourier transform of a measured spectrum, with power as a function of inverse wavelength (wavenumber).

The controller 190, e.g., the computing device, can be programmed to perform a Fourier transform of each measured spectrum to generate a sequence of transformed spectra. Each transformed spectrum from the sequence of transformed spectra is the Fourier transform of an associated measured spectrum from the sequence of measured spectra. The Fourier transform can be a fast Fourier transform (FFT). FIG. 4 illustrates an example of a Fourier transform 320 of a measured spectrum, in particular a Fourier transform of the measured inverse wavelength spectrum.

The Fourier transform of an inverse wavelength spectrum will yield peaks in the Fourier space. This is advantageous because the position of the peaks in the Fourier space can be in units of length, the same as the units of the thickness of the layer. By performing the Fourier transform on the inverse wavelength spectrum, the x-axis in the Fourier space will have units of thickness (e.g. micrometers). For example, the position of the peaks can be in units of nanometers.

The peaks can correspond to the thickness of each layer in the stack. For each layer, there will be a peak in Fourier space with a position on the x-axis (i.e., on the length axis) that indicates the thickness of the layer. For example, referring to FIG. 4, the Fourier transform 320 includes multiple peaks 322. It may be possible to convert the position of the peak in the Fourier transform into an absolute thickness of the layer. In order to make such a conversion, a scale factor is required. The scale factor can depend on the material type. For example, there can be a scale factor for the adhesive layer and a different scale factor for the silicon layer. The scale factor will depends on various optical properties of the material (n, k, angle of incidence), as well as on the optical properties of the adjacent layer. The scale factor can be determined empirically. For example, another metrology technique, e.g., transmission electron microscopy (TEM), can be used to obtain a reliable measurement of the thickness of a layer of a test substrate. The ratio between the position value of the peak and the measured thickness provides the scale factor.

Figure 5:
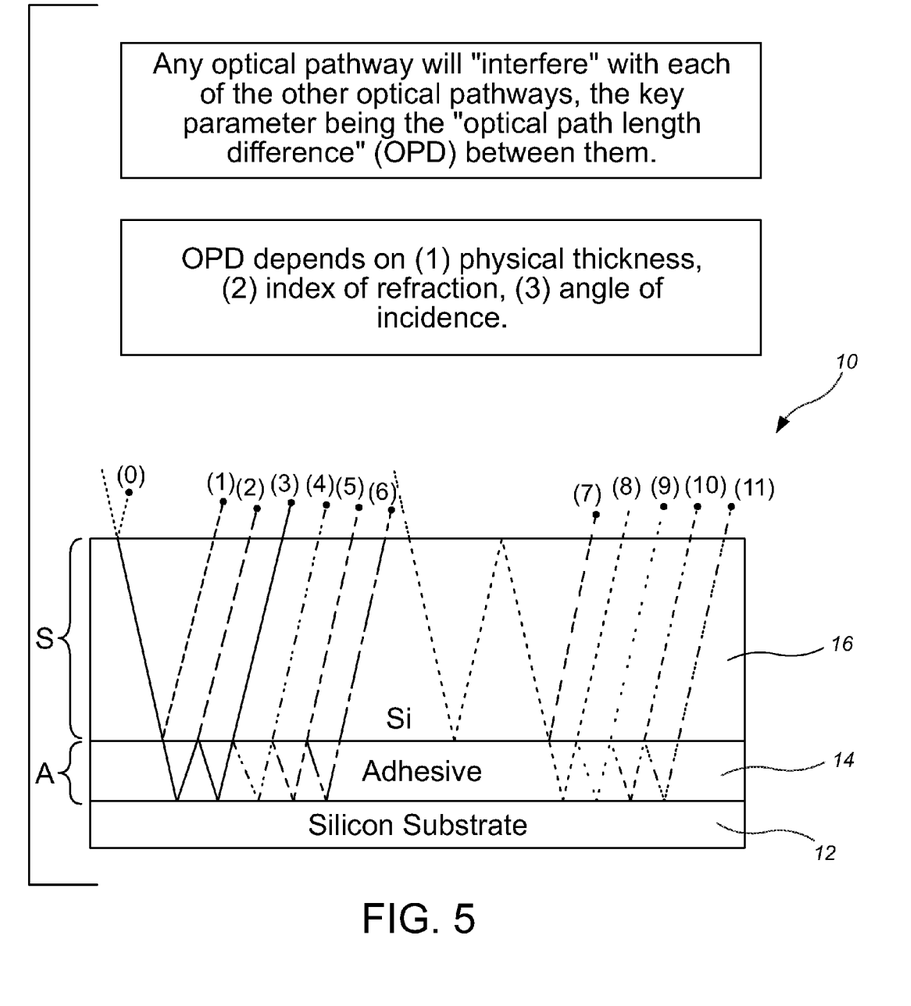
FIG. 5 illustrates a layer stack of a substrate in a TSV fabrication process.

Due to the multiple reflections at various interfaces of the stack, particularly for substrates that include complex layer stacks, there can be additional peaks in the Fourier transform. For example, FIG. 5 illustrates a layer stack of a substrate 10 in a TSV fabrication process. The substrate 10 includes a silicon wafer 12, a silicon layer 16 with a thickness S, and adhesive layer 14 with a thickness A that secures the silicon layer 16 to the silicon wafer 12.

Where there are multiple peaks, one of the multiple peaks can be selected as a peak of interest. The peak of interest is typically the peak with the position that corresponds to the thickness of the layer being polished.

Each possible optical pathway can generate a separate peak in the Fourier transform. The Fourier transform tends to include clusters of peaks that correspond to the various layers. The peak of interest is typically the primary peak in a cluster, e.g., the $0^{th}$ order harmonic peak. The primary peak should be generated by interference between two light paths generated by reflections from the top and bottom of the layer, without reflections from other boundaries. Other peaks in the cluster can be caused by interference between light paths that include reflections from other boundaries.

If the clusters are separate, then the peak of interest is typically the highest peak in the cluster. However, noise and distortion from pattern effects or from sublayer effects can make the primary peak lower in height than one of the harmonics in the cluster. In addition, if the clusters overlap, then peaks cause by higher harmonics, e.g., $1^{st}$ order harmonic peaks or higher, can be used to determine the primary peak.

In general, to identify the peak of interest, peaks that fall within a predetermined range of position values are identified. Then, one of the peaks can be selected based on the relative height and position of the peaks within the range. The logic to select the peak of interest can be stored in the controller 190. In some implementations, the highest peak and the second highest peak in the predetermined position range are identified. The predetermined position range can be input by a customer or manufacturer of the software. The positions of the peaks (in units of thickness) and the heights of the peaks within the predetermined position range are determined. The position of a peak can be determined from the x-axis position at the maximum amplitude of the peak.

Figure 6:
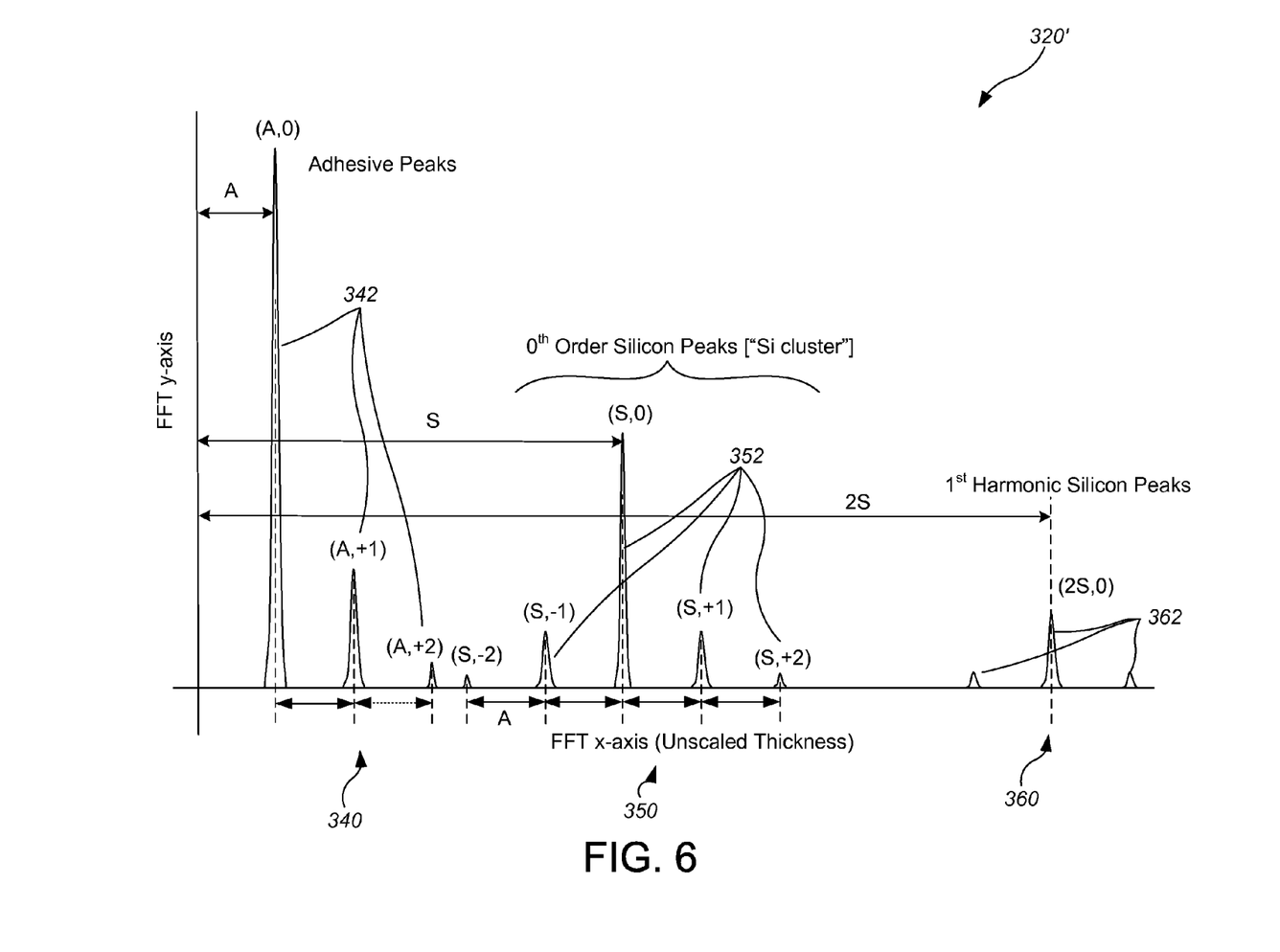
FIG. 6 illustrates an idealized Fourier transform of a measured inverse wavelength spectrum from the substrate of FIG. 5.

For example, referring to FIG. 6, the Fourier transform 320' includes a first cluster 340 of peaks 342, the (A,0), (A,+1), (A,+2) peaks. The first cluster 340 can be the result of optical paths that have one or more reflections in the adhesive layer 14. Each peak 342 in the first cluster 340 can be separated by a distance that depends on the thickness A of the adhesive layer 14.

Fourier transform 320' includes a second cluster 350 of peaks 352. The second cluster 350 can include peaks 352 that are the result of optical paths that have one reflection in the silicon layer 14, i.e., be the $0^{th}$ order silicon peaks. The primary peak, i.e., the (S,0) peak, is generated by interference between reflections from the top and bottom of the silicon layer. Other peaks in the cluster 350, illustrated as the (S,−2), (S,−1), (S,+1), (S+2) peaks, can be caused by interference between light paths that include reflections from other boundaries. Each peak 352 in the second cluster 350 can be separated by a distance that depends on the thickness A of the adhesive layer 14.

The primary peak 354 in the second cluster 350, i.e., the (S,0) peak, can have an a-axis value that depends on the thickness S of the silicon layer 16. In theory, the highest peak is the highest peak in the cluster. In practice, due to noise and distortion from pattern or sublayer effects, the (S,0) peak may not be the highest peak in the cluster. The logic for properly assigning peaks must consider this possible distortion.

The third cluster 360 can include peaks 362 that are the result of optical paths that have two reflections in the silicon layer 14, i.e., be the 1st harmonic silicon peaks. In general, the largest 1st harmonic silicon peak, i.e., the (2S,0) peak, will have twice the position value of the $0^{th}$ order silicon peak.

FIG. 6 illustrates an idealized graph, but it may be difficult to identify the peak of interest for the layer being polished, e.g., the (S,0) peak, due to the clusters of peaks overlapping and/or the noise in the signal.

In order to identify the peak of interest for the layer being polished, the controller can be programmed with a logic pathway to automatically select one of the peaks. In general, first, peaks that fall within a predetermined position range are identified. Then, one of the peaks can be selected based on the relative height and position of the peaks within the range.

Figure 7:
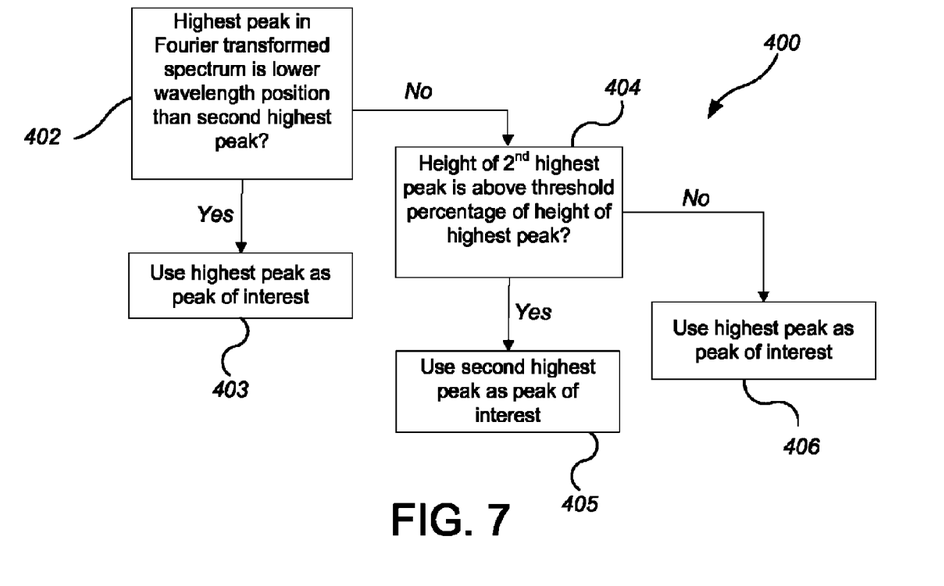
FIG. 7 illustrates a method of selecting a peak for tracking

FIG. 7 is a flowchart of a process 400 for selection of a peak. This process 400 is particularly applicable to polishing of a substrate from a TSV process, e.g., the substrate as illustrated in FIG. 5. However, it should be understood that for polishing of substrates with other layer configurations, it may be necessary to experiment and determine the selection logic empirically.

In the example of FIG. 7, the highest peak and the second highest peak in the predetermined position range are identified, and the positions of the peaks (in length units) and the heights of the peaks are determined. The height of a peak can be determined from the amplitude at the center of the peak.

Whether the highest peak is left of the $2^{nd}$ highest peak, i.e., if the highest peak has a smaller position value (in length units) than the $2^{nd}$ highest peak, is determined (step 402). If the highest peak has a smaller position value (in length units) than the $2^{nd}$ highest peak, then the highest peak is designated as the peak of interest, e.g., the (S,0) peak for the TSV process (step 403). If not, then the highest peak has a larger position value (in length units) than the $2^{nd}$ highest peak. In this case, whether the height of the second highest peak is above a preset threshold of the height of the highest peak, e.g., 70-90% of the magnitude of the highest peak, is determined (step 404). If the second highest peak is above a preset threshold of the height of the highest peak, then the second highest peak is designated as the peak of interest (step 405). If the second highest peak is left of the highest peak and is below the preset threshold of the highest peak, then the highest peak is designated as the peak of interest (step 406). The preset threshold can be set by the user prior to polishing.

Once the peak of interest for the layer being polished is selected, the position value, e.g., the length unit position value, of the peak of interest is determined. By determining the position value for the peak of interest for each transformed spectrum of the sequence, a sequence of position values is generated.

Figure 8:
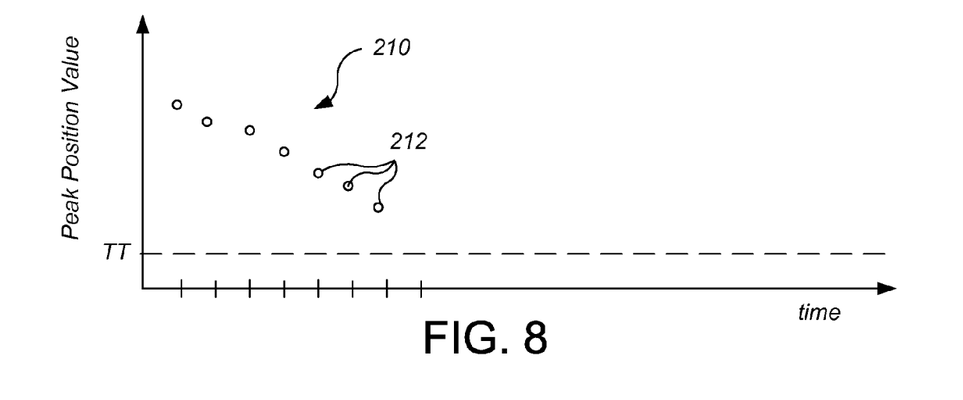
FIG. 8 illustrates a sequence of values from the selected peak.

Referring to FIG. 8, which illustrates the results for only a single zone of a substrate, the sequence of position values generated by determining the position value for each measured spectrum in the sequence of measured spectra generates a time-varying sequence of position values 212. This sequence of position values can be termed a trace 210. In general, for a polishing system with a rotating platen, the trace 210 can include one, e.g., exactly one, position value per sweep of the optical monitoring system below the substrate. If multiple zones are monitored, there can be one position value per sweep per zone.

In some implementations, polishing can be halted when the trace crosses a predetermined threshold value, e.g., the most recently generate value from the sequence of values is equal to or less than the predetermined threshold value. The predetermined threshold value can be determined empirically, e.g., by measuring the pre-polish and post-polishing thickness of a layer of a test substrate using a separate stand-alone metrology system, and comparing the results to of the comparing the sequence of values generated from the in-situ monitoring system during polishing of the test substrate.

Figure 9:
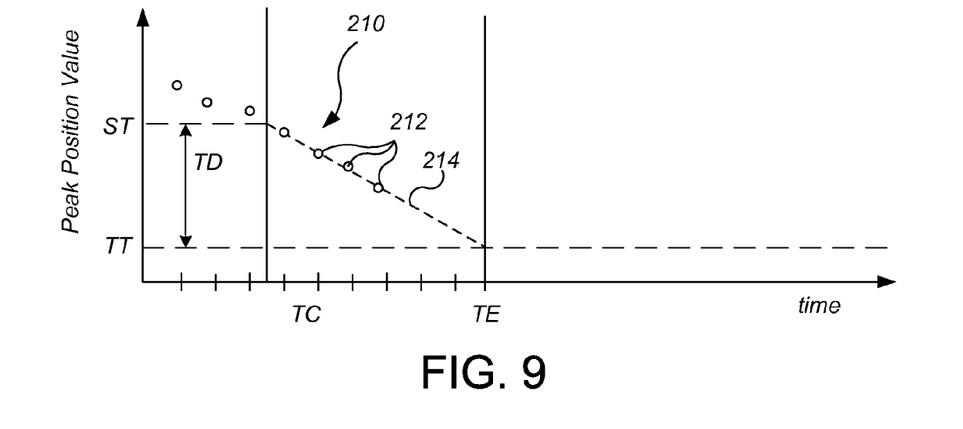
FIG. 9 illustrates a sequence of values having a linear function fit to the index values.

Optionally, as shown in FIG. 9, a function, e.g., a polynomial function of known order, e.g., a first-order function (e.g., a line 214), is fit to the sequence of position values, e.g., using robust line fitting. Other functions can be used, e.g., polynomial functions of second-order, but a line provides ease of computation.

Optionally, the function can be fit to the position values collected after time a TC. Position values for spectra collected before the time TC can ignored when fitting the function to the sequence of position values. This can assist in elimination of noise in the measured spectra that can occur early in the polishing process, or it can remove spectra measured during polishing of another layer.

Figure 10:
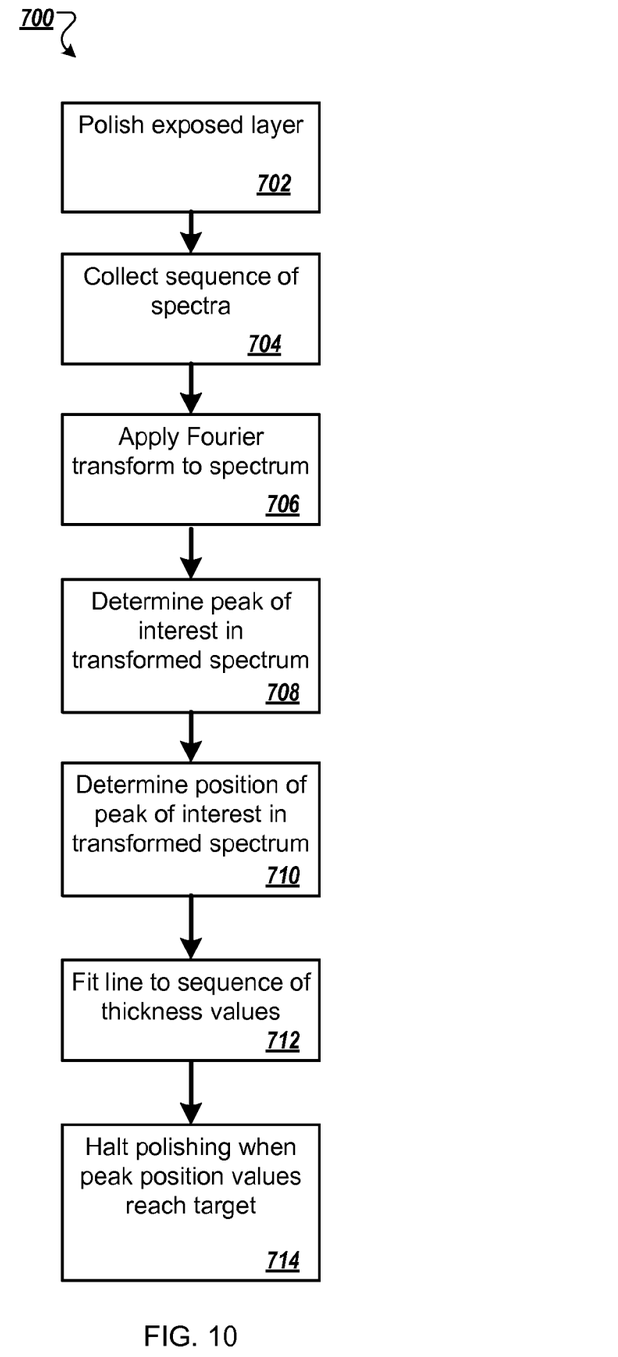
FIG. 10 is a flow diagram of an example process for controlling a polishing operation.

FIG. 10 shows a flow chart of a method 900 of polishing a product substrate. The product substrate can have at least the same layer structure as what is represented in the optical model.

The product substrate is polished (step 702), and a sequence of measured spectra are obtained during polishing (step 704), e.g., using the in-situ monitoring system described above. There may be a variety of preliminary polishing steps prior to obtaining the sequence of measured spectra. For example, one or more overlying layers can be removed, e.g., a conductive layer or dielectric layer, and measuring of the spectra can be triggered when removal of an overlying layer. For example, exposure of the first layer at a time TC (see FIG. 9) can be detected by a sudden change in the motor torque or total intensity of light reflected from the substrate, or from dispersion of the collected spectra.

A Fourier transform is applied to each measured spectrum in the sequence to generate a transformed spectrum, thereby generating a sequence of transformed spectra (step 706). The measured spectrum can have intensity as a function inverse wavelength, so the transformed spectrum can have intensity as a function of length, e.g., thickness. For each transformed spectrum in the sequence of transformed spectra, a peak of interest is determined (step 708), and the position which is in length units, of the selected peak of the transformed spectrum is determined (step 710), thereby generating a sequence of position values. The position of the peak can be considered as the x-axis value of the peak on a graph of the Fourier transform.

The endpoint can be determined from the sequence of peak position values (step 714). For example, polishing can be halted when the most recently generated value from the sequence of peak position values crosses a predetermined threshold value (step 714). The target position value TT can be set by the user prior to the polishing operation and stored. Alternatively, a target amount to remove can be set by the user, and a target position value TT can be calculated from the target amount to remove. For example, a thickness difference TD can be calculated from the target amount to remove, e.g., from an empirically determined ratio of amount removed to the position valued, and adding the thickness difference TD to the starting position value ST. The starting position value ST can be the position value at the time TC that clearance of the overlying layer is detected (see FIG. 9). As noted above, a function can be fit to the sequence of peak position values (step 712) and the time TE at which the linear function will equal the target position value TT can be calculated, although this is optional. Polishing is halted when the peak position values reach the target position value TT (step 714).

It is possible to generate a sequence of position values for different zones of the substrate, and use the sequences from different zones to adjust the pressure applied in the chambers of the carrier head to provide more uniform polishing, e.g., using techniques described in U.S. application Ser. No. 13/096,777, incorporated herein by reference (in general, the position value can be substituted for the index value to use similar techniques). In some implementations, the sequence of position values is used to adjust the polishing rate of one or more zones of a substrate, but another in-situ monitoring system or technique is used to detect the polishing endpoint.

In addition, although the discussion above assumes a rotating platen with an optical endpoint monitor installed in the platen, system could be applicable to other types of relative motion between the monitoring system and the substrate. For example, in some implementations, e.g., orbital motion, the light source traverses different positions on the substrate, but does not cross the edge of the substrate. In such cases, measured spectra can be collected at a certain frequency, e.g., 1 Hz or more.

Figure 11A:
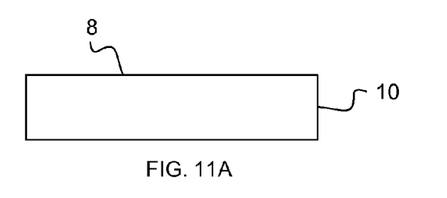
FIGS. 11A-11H illustrate a method of forming a through-silicon via (TSV).
Figure 11B:
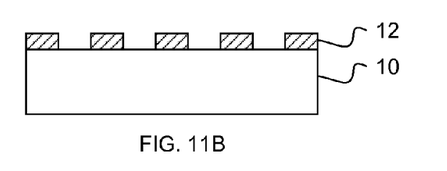
Figure 11C:
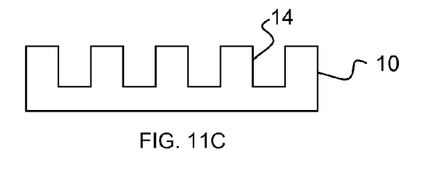
Figure 11D:
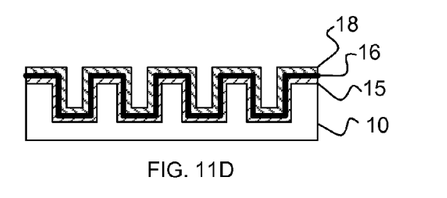
Figure 11E:
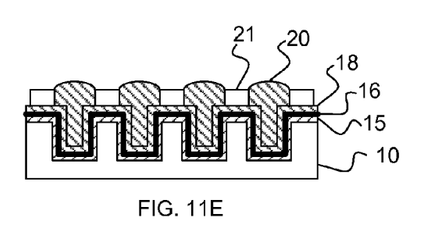
Figure 11F:
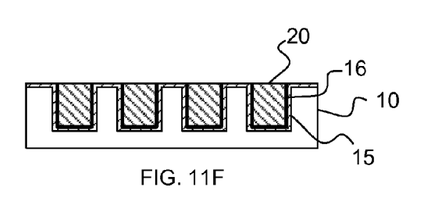
Figure 11G:
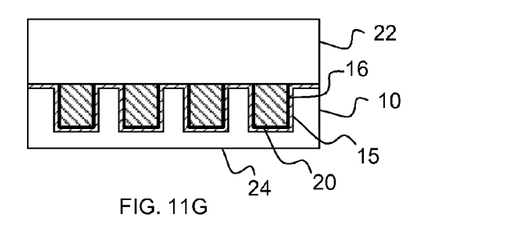
Figure 11H:
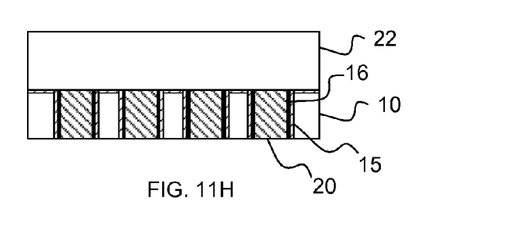

As noted above, an example of an application that has a thick layer being polished and multiple layers in the stack is fabrication of a through-silicon via (TSV). Fabrication of a semiconductor chip including TSVs begins by coating a front side 8 of a silicon substrate 10 (see FIG. 11A) with a photoresist layer 12, and patterning the photoresist layer 12 (see FIG. 11B). An anisotropic etch is performed using the patterned photoresist layer 12 as a mask, forming a plurality of recesses 14 that extend partially but not entirely through the silicon substrate 10 (see FIG. 11C). The surface of the silicon substrate 10 (including in the recesses 14) can be oxidized to form an oxide liner 15, a barrier layer 16 can be deposited on the oxide liner 15, and a seed layer 18 can be deposited on the barrier layer 16 (see FIG. 11D). The recesses in the silicon substrate 10 are then filled, e.g., by electroplating, with a conductive layer 20, e.g., copper (see FIG. 11E). An insulative layer 21 can be disposed over portions of the top surface of the seed layer 16 so that electroplating is generally constrained to the recesses 14. Alternatively, it may be possible to deposit the conductive layer 20 without first depositing a seed layer, e.g., by vapor deposition process. The portions of the conductive layer 20 that form on the top surface of the silicon substrate 10 can be removed by chemical mechanical polishing, leaving conductive pillars 20 in the recesses (see FIG. 11F). Although FIG. 11F illustrates a portion of the oxide liner 15 remaining on the exposed surface, polishing could be halted once the silicon substrate 10 is exposed, or while the barrier layer 18 is exposed (assuming that the barrier layer is non-conductive). The silicon substrate 10 can then be bonded to a carrier substrate 22 (see FIG. 11G), and the back side 24 of the silicon substrate can then be thinned, e.g., by chemical mechanical polishing, until the conductive pillars 20 are exposed, thus leaving the conductive pillars 20 as vias through the silicon substrate 10 (see FIG. 1H). Further processing can be performed on the back-side of silicon substrate 10. In addition, other thin layers may be present on the frontside of the TSV substrate, such as active devices and interconnects, that are not directly involved or removed by our CMP processes being described.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., the substrate can be a bare wafer, or it can include one or more deposited and/or patterned layers. The term substrate can include circular disks and rectangular sheets.

Embodiments of the invention and all of the functional operations described in this specification can be implemented in digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in a non-transitory machine readable storage media, for execution by, or to control the operation of, data processing apparatus, e.g., a programmable processor, a computer, or multiple processors or computers.

The above described polishing apparatus and methods can be applied in a variety of polishing systems. Either the polishing pad, or the carrier heads, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation.

Particular embodiments of the invention have been described. Other embodiments are within the scope of the following claims.

What is claimed is:

1. A method of controlling a polishing operation, comprising:
    polishing a substrate;
    during polishing, obtaining a sequence over time of measured spectra from the substrate with an in-situ optical monitoring system;
    for each measured spectrum from the sequence of measured spectra, applying a Fourier transform to the measured spectrum to generate a transformed spectrum thus generating a sequence of transformed spectra;
    for each transformed spectrum, selecting a peak of interest from a plurality of peaks in the transformed spectrum, wherein selecting the peak of interest includes identifying a highest peak and a second-highest peak within a range of position values, determining a height and a position for each of the highest peak and the second-highest peak, and determining whether the highest peak has a lower position value than the second-highest peak;

for each transformed spectrum, determining a position value for the peak of interest in the transformed spectrum thus generating a sequence of position values; and determining at least one of a polishing endpoint or an adjustment of a pressure to the substrate from the sequence of position values.

2. The method of claim 1, wherein obtaining the sequence of measured spectra comprises directing a beam of near infrared light onto the substrate and measuring a spectrum of a reflection of the beam.

3. The method of claim 2, wherein the beam of near infrared light comprises light having a wavelength of 0.9 to 1.7 μm.

4. The method of claim 2, wherein polishing the substrate comprises a polishing step in fabrication of a through silicon via.

5. The method of claim 1, wherein polishing the substrate comprises a polishing step in fabrication of a through silicon via.

6. The method of claim 5, wherein polishing the substrate comprises polishing a silicon layer of a multilayer substrate, the multilayer substrate including a semiconductor wafer and an adhesive layer bonding the silicon layer to the semiconductor wafer.

7. The method of claim 1, wherein polishing the substrate comprises polishing an overlying first layer of a multilayer substrate, the multilayer substrate including an underlying second layer and a third layer, the second layer between the first layer and the third layer.

8. The method of claim 7, wherein the first layer has a thickness greater than two microns.

9. The method of claim 1, wherein applying a Fourier transform comprises applying a fast Fourier transform.

10. The method of claim 1, wherein the measured spectrum is a spectrum of intensity as a function of wavenumber and the transformed spectrum is a spectrum of intensity as a function of length.

11. The method of claim 1, wherein selecting the peak of interest includes determining that the highest peak has a lower position value than the second-highest peak and the highest peak is selected as the peak of interest.

12. The method of claim 1, wherein selecting the peak of interest includes determining whether the height of the second-highest peak is within a threshold of the height of the highest peak.

13. The method of claim 12, wherein selecting the peak of interest comprises determining that the highest peak has a higher position value than the second-highest peak and that the height of the second-highest peak is above a threshold of the height of the highest peak and the highest peak is selected as the peak of interest.

14. The method of claim 12, wherein selecting the peak of interest comprises determining that the highest peak has a higher position value than the second-highest peak and that the height of the second-highest peak is below a threshold of the height of the highest peak and the second-highest peak is selected as the peak of interest.

15. The method of claim 12, wherein polishing the substrate comprises polishing a silicon layer of a multilayer substrate, the multilayer substrate including a semiconductor wafer and an adhesive layer bonding the silicon layer to the semiconductor wafer.

16. The method of claim 12, wherein the position value is in units of length.

17. The method of claim 16, wherein the position value comprises a thickness.

* * * * *